United States Patent [19]

Steer

[11] Patent Number: 4,755,377

[45] Date of Patent: Jul. 5, 1988

[54] FOAMED AIR FRESHENER COMPOSITION

[75] Inventor: Frank J. Steer, Fort Wright, Ky.

[73] Assignee: The Drackett Company, Cincinnati, Ohio

[21] Appl. No.: 42,122

[22] Filed: Apr. 24, 1987

[51] Int. Cl.$^4$ .......................... A61L 9/01; A61K 7/46; B01J 13/00

[52] U.S. Cl. .................. 424/76.4; 424/76.3; 239/60; 252/315.3; 512/4

[58] Field of Search .............. 424/76.3, 76.4; 239/60; 252/315.3; 512/4

[56] References Cited

U.S. PATENT DOCUMENTS

| | | | |
|---|---|---|---|
| 2,691,615 | 10/1954 | Turner et al. ................. | 424/76.3 X |
| 2,927,055 | 3/1960 | Lanzet ........................... | 424/76.4 X |
| 3,956,173 | 5/1976 | Towle ............................ | 424/76.3 X |
| 3,969,280 | 7/1976 | Sayce et al. ................... | 424/76.4 X |
| 3,997,480 | 12/1976 | Singleton et al. ............. | 424/76.4 X |
| 4,056,612 | 11/1977 | Lin .................................. | 424/76.3 |
| 4,071,616 | 1/1978 | Bloch ............................. | 424/76.4 |
| 4,128,507 | 12/1978 | Mitzner ......................... | 424/76.4 X |
| 4,178,264 | 12/1979 | Streit et al. ................... | 424/76.3 X |
| 4,318,746 | 3/1982 | Claffey et al. ............... | 106/194 |

Primary Examiner—John E. Kittle
Assistant Examiner—Susan S. Rucker
Attorney, Agent, or Firm—Charles J. Zeller

[57] ABSTRACT

An aqueous-based gel air-treating composition comprising a gel base including a gel-forming agent and a gaseous component in an amount effective to provide a bulk density of said composition of from about 0.5 to about 0.9 g/cc, the gaseous component being present in within the composition as substantially homogeneously dispersed bubbles having a diameter of less than about 3000 microns, the composition being obtained by preparing said gel base, introducing the gaseous component into said gel base with sufficient mixing energy to obtain a foamed gel, and allowing the foamed gel to cool below its glass transition temperature.

21 Claims, No Drawings

FOAMED AIR FRESHENER COMPOSITION

FIELD OF INVENTION

The present invention relates to aqueous-based gel air-treating compositions and to their method of manufacture. More specifically, the present invention concerns the improvement in such air-treating compositions, wherein a gaseous component is introduced into the gel base prior to cooling, the resulting product exhibiting an improved transmission efficiency with time of the perfume constituents into the environment.

BACKGROUND OF THE INVENTION

Gelled air-treating compositions are known. See, for example, U.S. Pat. No. 2,691,615 to Turner, et al.; 2,927,055 to Lanzet; 3,969,280 to Sayce, et al.; 3,997,480 to Singleton, et al.; 3,956,173 to Towle; 4,056,612 to Lin; 4,071,616 to Bloch; 4,128,507 to Mitzner; 4,178,264 to Streit, et al., and 4,318,476 to Claffey et al.

A disadvantage of the conventionally gelled air-treating compositions, however, is their inefficiency in regard to perfume release. It has been found that large amount, often 30% by weight or more of the volatile perfume components incorporated in the prior art gel products during manufacture, in fact, is not released to the environment, but rather is entrapped in a gel residue. Thus, at the point the consumer can no longer detect a noticeable release of perfume, the product is discarded by the consumer, even though the gel residue contains undiffused fragrance. Beneficially, the gelled air freshner dispensers should provide essentially complete utilization of the perfume with adequate levels dispensed from the gel composition during its useful life.

It is an object, then, of the present invention to provide an aqueous-based gel air-treating composition that exhibits improved fragrance transmission efficiency during its useful life.

It is a further object of the present invention to substantially reduce the concentration of the volatile perfume constituents remaining in the residue portion of the gel at the end of its useful life.

Another object of the present invention is to provide an aqueous-based gel air-treating composition that exhibits greater fragrance-release per unit weight of product at a given perfume load.

To achieve the aforesaid objects, it is primarily an object of the present invention to provide an aqueous-based gel air-treating composition which incorporates air or other inert gaseous material into its gel base composition.

Yet another object of the present invention is to provide a method for the manufacture of the air-treating composition of the present invention.

These and other objects and advantages will be more readily apparent upon reading the detailed description of the invention, a summary of which follows.

SUMMARY OF THE INVENTION

The aqueous-based gel air-treating compositions of the present invention comprise (a) a gel base including gelling agent, water and perfume, and (b) a gaseous component, said gaseous component being included in an amount effective to reduce the bulk density of the gel base by from about 10 to about 50%, the gaseous component being present within the product composition as substantially homogeneously dispersed bubbles, bulk density being measured at 20° C. That is, the air treating compositions of the present invention have a bulk density at 20° C. of from about 0.5 to about 0.9 g/cc.

The gel base comprises by weight of said substrate from about 0.5 to about 10% of a gel-forming agent, on an anhydrous basis; water in an amount effective to subsequently hydrate said gel-forming agent; and from about 0.2 to about 5% of said perfume constituent. Suitable gel-forming agents include carrageenan, algins, agars, and other carbohydrates such as amylose, and trivalent metal complexes of carboxymethyl cellulose as disclosed in U.S. Pat. No. 3,969,280 to Sayce, et al. Suitable gaseous components are air, nitrogen, carbon dioxide, and the noble gases. Generally, bubbles having a diameter of greater than 3,000 microns will not be present in the compositions of the present invention, the mean bubble diameter being between about 50 to about 1000 microns. Most preferably, the mean bubble diameter is about 150 microns, the one sigma distribution of the bubbles in this embodiment being from about 100 to about 200 microns and the three sigma distribution incorporating bubbles having a diameter of less than about 300 microns.

The compositions of the present invention preferably include up to about 5% of a viscosity control agent, and may further include as other optional constituents gelling aids such as potassium chloride, humectants, perfume fixatives, extenders, preservatives, freeze-thaw stabilizers, and dye.

DETAILED DESCRIPTION OF THE INVENTION AND PREFERRED EMBODIMENT

Aqueous-based gel air-treating products are sold to consumers or end-users in a sealed container, generally of attractive design, within which is contained the gel air-treating composition. The container often includes means for adjustably exposing all or a desired portion of the composition to the environment, and the opened container is placed by the consumer in a convenient location. The product includes a sufficient weight of the gelled air-treating composition to provide a useful life of approximately 4 to 8 weeks, depending upon such factors as air movement, humidity, and temperature, as well as the area of the opening set by the consumer. observation of the prior art products towards the end of their useful lives will reveal that there is a drop in the fragrance emission to the environment. A dry and brittle residue of the composition, generally from about 10 to about 20% by weight of the initial weight of the composition, remains at the end of the product's life. An analysis of this residue shows that a large percentage, often 30% or more of the volatile perfume components based on the initial weight of the volatile perfume components, remains entrapped therein.

The reasons for such inefficient perfume release from the conventional aqueous-based gel air-treating products are several. During manufacture the perfume oil is dispersed as microdroplets in a continuous aqueous phase. During use the perfume components have an inherently limited driving force to effect diffusion from the dispersed oil phase into the hydrated gel medium and ultimately from the hydrated gel medium into the environment. Second, as the gel dries, a surface film layer of a rigid, hydrated gel is formed, and the perfume droplets therewithin exhibit less and less tendency to diffuse through this "skin" to the atmopshere. Third, as the conventional gels evaporate, the surface area of the composition is reduced, again slowing the rate of perfume escape.

It has been found that the above-mentioned disadvantages and drawbacks of the conventional gel compositions may be avoided and/or mitigated by introducing air or other inert gaseous material in the form of small bubbles into the composition during gellation, the final product composition having a bulk density that is from about 10 to about 50% less than the density of the gel obtained in the absence of gasification.

By the practice of the above method, a major portion of the perfume oil previously residually entrapped in the prior art compositions is diffusable into the environment. Although a surface film layer will form as a result of water evaporation from the gel, the porosity of the composition of the present invention mitigates greatly the detrimental effect of the "skin" formation. Moreover, introduction of the gas into the gel base compositions of the present invention results in a porous, recticulated structure, and the surface of the gel, both initially and during use, is characterized by a large surface area, which helps maintain the rate of diffusion of the perfume oil during use. Thus, it has been found that products made according to the method of the present invention provide excellent air-freshening capacity per unit weight of perfume contained in the composition.

The aqueous-based gel air-treating compositions of the present invention thus comprise (a) a gel base composition including gelling agent, water, and perfume and (b) a gaseous component included in the gel base composition in an amount effective to provide said aqueous-based gel air-treating composition which has a bulk density that is from about 10 to about 50% lower than the bulk density of a product obtained from said gel base composition in the absence of gas incorporation, density being measured at 20° C., the gaseous component being present within the air-treating composition of the present invention as substantially homogeneously dispersed bubbles. At less than a 10% bulk density reduction, there is no noticeable improvement in performance, while at more than about 50% density reduction, the product loses its ability to maintain its integrity. As used herein with respect to compositions of the present invention, the term "gel base composition" or "gel base" refers to the mixture of components from which the gel is made. The "gel base" is aerated prior to cooling. "Aeration" and "aerated" as used herein refer to the incorporation of a suitable gas into the gel base. "Composition" and "product composition" refer generally to the composition or product of the present invention, that is, the cooled, aerated gel base composition.

Typically, the compositions of the present invention have a bubble size distribution such that the mean bubble size will be between about 50 to about 1000 microns, with the one sigma distribution being from about ±200 to about ±400 microns, and the three sigma distribution being from about ±600 to about ±1200 microns.

As a rule, the gas bubbles have a maximum diameter of about 3,000 microns. Preferably, the gas bubbles have a diameter of less than about 1,000 microns, and preferably range between about 25 to about 600 microns. In an especially preferred embodiment, the mean bubble diameter is about 150 microns, the one sigma distribution being ±50 microns and the three sigma distribution being ±150 microns. It should be understood that forces acting on the bubbles during gellation, mixing and cooling may tend to distort their shape, especially for the larger diameter bubbles.

The gel base composition comprises by weight of said gel base from about 0.5 to about 10% of a gel-forming agent, on an anhydrous basis; water in an amount effective to substantially hydrate, i.e., gel, said gel-forming agent, and from about 0.2 to about 5% of said perfume constituent.

The gel-forming agent may be any such material used in the preparation of the conventional compositions, and includes carrageenan, agars, algins, and other carbohydrates typically used for such gelled products such as amyloses, and trivalent metal complexes of carboxymethyl cellulose. These gel-forming agents are preferably included in the gel base in an amount of from about 0.5 to about 10% by weight of the gel base composition, most preferably in an amount of from about 1.0 to about 2.5% of the base composition. Carrageenan is an especially preferred gel-forming agent. A preferred gelling agent is Genugel sold by Marine Colloids, which material is a proprietary mixture of carrageenans, as well as gums, sugars, and trace levels of mono- and divalent ions.

The perfume constituent is suitably any volatile organic natural compound an mixture of compounds, typically essential oils obtained from leaves, flowers, fruits, roots and wood; from animal sources, and from resinous extracts, capable of imparting a pleasing fragrance. Mention may be made, by way of example, of oil of rose, oil of lime, oil of pine, oil of wintergreen, and the like. Synthetically derived fragrancing materials, for example esters, aldehydes and ketones, may also be used as the perfume constituent, typically in admixture or in admixture with the natural substances. Synthetically obtained compounds also include the synthetically prepared oderiferous active materials of the essential oils. The perfume constituent is frequently a complex mixture of one or of such more essential oils and/or synthetic fragrancing materials, and is typically available from a commercial perfume supplier. The perfume constituents are often provided in a suitable vehicle, for example, a alcoholic or other solvent. In lieu of or in addition to the perfume constituent, the gel compositions of the present invention may include other volatile air treating constituents known to the art, for example, pheromones, bactericides, insect attractants and repellants, animal attractants and repellants, insecticides, fungicides, and pharmaceutical and vetinary drugs. Suitable levels of the air-treating constituents range from 0.2 to 5%, preferably from about 0.5 to about 2%, by weight of the base composition.

Preferably, the gel base composition includes a viscosity control agent to reduce creaming of the air bubbles in the aerated gel sol and to aid in the control of syneresis, as described in greater detail below with respect to the method of manufacture. These viscosity-control agents include the water-soluble cellulose derivatives, for example, carboxymethyl cellulose; naturally occurring plant extracts such as xanthan, locust bean gum, guar gum, and the mineral-derived thickeners such as laponite and bentonite clays. Especially preferred are viscosity-control agents that produce a yield value or show thixotropic rheology. These viscosity-control agents generally are included at levels up to about 3.0% by weight of the gel base composition, preferably from about 0.10 to about 1.0%. The preferred viscosity-control agent is carboxymethyl cellulose.

It is also preferred to include a surface-active or foaming agent in the gel base composition to reduce the interfacial tension between the liquid and the gas. Thus, the air is more easily incorporated within the aqueous gel. Any conventional foaming agent including most nonionic, anionic, cationic, amphoteric, or zwitterionic surfactants may be used for this purpose, provided, of course, that such foaming agent is compatible with the gel system. Also suitable are natural products, such as sugar derivatives, especially sucrose esters, that show surface activity. The anionic and nonionic surfactants are preferred, in view of their ready availability, compatability and cost.

Broadly, the anionic surfactants are water-soluble alkyl or alkylaryl compounds, the alkyl having from about 8 to about 22 carbons, including a sulfate or sulfonate substituent group that has been base-neutralized, typically to provide an alkali metal, e.g., sodium or potassium, or an ammonium anion, including, for example: (1) alkyl and alkylaryl sulfates and sulfonates having preferably 10 to 18 carbons in the alkyl group, which may be straight or branched chain, e.g., sodium lauryl sulfate and sodium dodecylbenzene sulfonate; (2) alpha-olefin aryl sulfonates preferably having from about 10 to 18 carbons in the olefin, e.g., sodium $C_{14-16}$ olefin sulfonate, which is a mixture of long-chain sulfonate salts prepared by sulfonation of $C_{14-16}$ alpha-olefins and chiefly comprising sodium alkene sulfonates and sodium hydroxyalkane sulfonates; (3) sulfated and sulfonated monoglycerides, especially those derived from coconut oil fatty acids; (4) sulfate esters of ethoxylated fatty alcohols having 1–10 mols ethylene oxide, e.g., sodium polyoxyethylene (7 mols EO) lauryl ether sulfate, and of ethoxylated alkyl phenols having 10 mols ethylene oxide and 8 to 12 carbons in the alkyl, e.g., ammonium polyoxyethylene (4 mols EO) nonyl phenyl ether sulfate; (5) base-neutralized esters of fatty acids and isethionic acid, e.g., sodium lauroyl isethionate; (6) fatty acid amides of a methyl tauride, e.g., sodium methyl cocoyl taurate, (7) B-acetoxy- or B-acetamidoalkane sulfonates where the alkane has from 8 to 22 carbons, e.g., sodium lauroyl sarcosinate, and (8) base neutralized fatty acids, e.g., potassium stearate.

The nonionics include (1) fatty alcohol alkoxylates, especially the ethoxylates, wherein the alkyl group has from 8 to 22, preferably 12 to 18, carbons, and typically 6 to 15 mols alkoxide per molecule, e.g., coconut alcohol condensed with about nine mols ethylene oxide; (2) fatty acid alkoxylates having from about 6 to about 15 mols alkoxylate, especially the ethoxylate; (3) alkylphenoxy alkoxylates, especially the ethoxylates, containing 6 to 12 carbons, preferably octyl or nonyl, in the alkyl, and having about 5 to 25, preferably 5 to 15 mols alkylene oxide per molecule, e.g., nonyl phenol ethoxylated with about 9.5 mols ethylene oxide (e.g., Igepal CO-630); (4) condensates of ethylene oxide with a hydrophobic base formed by condensation of propylene oxide with propylene glycol, e.g., nonionic surfactants of the Pluronic series manufactured by BASF Wyandotte, (5) condensates of ethylene oxide with an amine or amide; (6) fatty amine oxides, e.g., stearyl dimethyl amine oxide, and (7) alkylolamides.

Preferred anionics are the alkyl and alkylaryl sulfates, the ethoxylated octyl and nonyl phenol sulfates and the alpha-olefin aryl sulfonates, while preferred nonionics are the fatty alcohol ethoxylates and the alkyl phenoxy ethoxylates.

The cationic surfactants include, for example, cetyl trimethyl ammonium chloride, which is a quaternary ammonium salt. The cationics are germicides, and a very minor concentration prevents growth of mildew and mold in the product. Of course, cationic surfactants should not generally be used in combination with anionic surfactants, gelling agents or thickness.

Of the amphoterics, mention may be made of the imidazoline-based surfactants, for example, cocoamidoimidazolinium.

The foaming agent may be included in an amount of up to about 10% by weight of the gel base composition, preferably from about 0.1 to about 5% by weight, most preferably from about 0.25 to about 2.5% by weight.

The compositions of the present invention may also include one or more adjuvants including, by way of example, gelling aids, preservatives, dyes, humectants, fragrance fixatives, emulsifiers, extenders, and freeze/thaw stabilizers such as the polyhydric alcohols and their esters. These materials are present in an amount effective to achieve their intended function, generally less than about 5% typically less than about 2%, by weight of the composition, although the freeze-thaw stabilizers, typically low molecular weight glycols and the like, might be included in amounts of up to about 10% by weight of the gel base.

The compositions of the present invention are obtained by first preparing the gel base composition in a batch or continuous feed process and during gellation of same introducing the gaseous material in such manner that gas bubbles will be uniformly distributed therewithin. The gel base can be obtained by mixing its several components into heated water under shear to form a sol, cooling the mixture to a temperature above its glass transition temperature to initiate gelling, and, during the gellation, introducing the gaseous material to obtain a foamed gel semifluid gel. Metered amounts of the foamed semifluid matrix are then dispensed into molds conforming to the shape of the final product composition, and allowed to cool to below its glass transition temperature. A batch continuous process wherein streams of the warm gel base composition and the gaseous material are combined followed by mixing at high shear is preferred. Any high shear mixing device for performing this step is acceptable, for example a Goodway mixer. It is preferred to keep the back pressure low to prevent too rapid an expansion of the bubbles resulting from the pressure drop across the pressure control valve in the line between the mixer and the dispensing nozzle.

The amount of air added to the gel base composition determines the degree of density reduction as compared to an unaerated gel, and is easily within the control of the processor. Typically, from about 0.1 to about 0.5 cc air/gm gel base at operating conditions is used for this purpose. Optimum efficiency in perfume release and without affecting product composition integrity is obtained at a 20 to 40% reduction in bulk density of the product compositions of the present invention as compared to that of the unaerated gel, density being measured at 20 °C.

Preferably, the gel base is prepared by forming a first premix comprising heated water, gelling agent, viscosity-control agent, and adjuvant to obtain a sol, which is thereafter cooled to less than about 140° F. A second premix comprising the surfactant and the perfume in aqueous solution is then added to the sol under conditions of shear. Advantageously, the viscosity-control agent controls the rate of creaming or frothing of the aerated mixture downstream of the aeration step and before the glass transition temperature is reached. The viscosity-control agent further aids in the control of syneresis wherein water would ordinarily be exuded from the gel sol prior to achieving the requisite substrate integrity, as the dispensed product composition cools.

The present invention is further illustrated by the examples which follow.

EXAMPLE 1

In a semicontinuous batch process, air freshener products in accordance with the present invention were made as follows, based on a 90-pound batch of the raw materials: In a jacketed tank, 1.75 parts Genugel AF carrageenan were mixed into heated water having a temperature of about 180° F. Mixing continued to ensure a uniform dispersion and adequate carrageenan hydration. To this sol was added 0.25 parts Hercules CMC-7H carboxymethyl cellulose, with mixing continuing to obtain a uniform dispersion, followed by addition of 2.9 parts Stepanol WA-C (29% solution of sodium lauryl sulfate). After dispersion thereof, mixing was discontinued for about three minutes, and cooling was effected by cold water circulating through the jacket. As the contents of the tank cooled, gellation occurred, and mixing reinstituted. When the temperature of the gelling composition reached about 135° F., 0.01 parts blue dye and 1.1 parts lemon oil perfume were added. The composition was then pumped from the tank at a flow rate of about 0.44 gal./min. This stream was combined with 60 psig dry air added at a flow rate of 0.11 gal./min. The aerated stream was then passed through a high energy mixing device, dispensed into suitable containers, and permitted to cool. Five representative samples (hereinafter Samples A) having an average intial weight of 167 grams and an average intial volume of 218 ml (average bulk density of 0.77 gms/ml) were selected from the units made and set aside for comparative testing. The initial perfume load was 1.84 grams per unit, and the initial perfume concentration was 1.1% by weight.

Using essentially the same procedure, five representative samples having an average weight of about 167 grams and a specific gravity of about 0.77 were set aside. These samples (hereinafter Samples B), on average, had an initial perfume load of 2.30 grams and an initial perfume concentration of 1.38% by weight, per unit.

The test Samples A and B above were comparatively tested for fragrance integrity performance against 218 gram unaerated control samples (hereinafter Control 1) having the composition:

| Control 1 | |
|---|---|
| Constituent | Weight (Grams) |
| Water | 209.53 |
| Carrageenan | 3.81 |
| Carboxymethyl cellulose[1] | 1.84 |
| Perfume | 2.39 |
| Dye and preservative | 0.02 |
| Total | 217.59 |

[1]CMC-7L, Hercules, Inc.

The specific gravity of the Control 1 samples was about 1.0, contained 2.39 grams perfume per unit, and had a perfume concentration of 1.1% by weight. As compared to the Control 1 samples, the Samples A contained less perfume but at equivalent concentration. As compared to the Control 1 samples, the Samples B contained essentially the same weight of perfume but at a higher concentration of perfume.

Sensory testing was conducted as follows: The five units of each of Samples A and B and of Control 1 were weighed and the average weight determined. The unit in each group A, B and Control 1 closest to the average weight within the group was each placed in a different room of 960 cubic feet and removed after 30 minutes. At least 12 judges with experience in olefactory evaluation were asked to rate blindly the intensity of the fragrance developed in each of the rooms, and their findings were averaged and normalized. The five units from each group were thereafter placed in a well-ventilated environment. After 21 days, the five units in each group were reweighed, and the unit closest to the average weight of the units in each group was returned to the separate rooms for a second intensity assessment. The procedure above was repeated after 35 days.

The findings are tabulated below.

| | Intensity* | | |
|---|---|---|---|
| Day | Sample A | Sample B | Control |
| 1 | 47.9 | 46.4 | 48.8 |
| 21 | 26.6 | 35.3 | 29.1 |
| 35 | 17.6 | 17.6 | 10.9 |

*Mean value of the judges, based on open ended scaling methodology. (0 = None; 100 = extemely intense).

It is seen that the Samples A and B were generally at or above parity as compared to Control 1 throughout the test period, and that after 35 days the Samples A and B made in accordance with the present invention were both superior to the Control 1.

As compared to Control 1, the Sample B units had at the commencement of the test about the same perfume load, about 20% greater perfume concentration, and about 20% less weight. As compared to Control 1, Sample A units had at the commencement of the test about the same perfume concentration, but about 23% less perfume by weight, and about 20% less total weight.

EXAMPLE 2

In a semicontinuous batch process, air freshener products in accordance with the present invention were made as follows, based on a 90-pound batch of the raw materials: In a jacketed tank, 2.0 parts Genugel AF carrageenan and effective amounts of dye and preservative were mixed into heated water having a temperature of about 180° F. Mixing continued to ensure a uniform dispersion and adequate carrageenan hydration. To this sol was added 0.30 parts Hercules CMC-7H carboxymethyl cellulose, with mixing continuing to obtain a uniform dispersion. Cooling to about 135° F. was effected by cold water circulating through the jacket, and 1 part of a premix of 25% Alipol CO 436 (a 58% active ammonium salt of a sulfated nonyl phenoxypoly (ethyleneoxy) ethanol) and 75% oriental type perfume oil was then added, followed by addition of 1.0 part Sipon L-22 (a 28% solution of ammonium lauryl sulfate). The composition was then pumped from the tank at a flow rate of about 0.50 gal/min. and combined with 60 psig dry air added at a flow rate of 0.125 gal/min. The aerated stream was passed through a high-energy mixing device, dispensed into suitable containers, and permitted to cool. Representative samples had, on average, a weight of about 177 grams and a volume of about 218 ml (i.e., a bulk density of about 0.8 g/cc). These samples contained about 1.33 grams perfume, and the air bubbles therein had a mean diameter of about 140 microns, with a one sigma distribution of ±50 microns.

Although the compositions and methods of the present invention have been described with reference to specific embodiments, these embodiments are illustrative only and not intended as limiting the scope of the invention as described in the appended claims.

I claim:

1. An aqueous-based gel air-treating composition comprising (a) a gel base including a gel-forming agent, water, and a volatile air-treating constituent, and (b) a gaseous component in an amount effective to provide a bulk density of said composition, measured at 20° C., of from about 0.5 to about 0.9 g./cc., the gaseous component being present within the composition as substantially homogeneously dispersed bubbles having a diameter of less than about 3,000 microns.

2. The composition of claim 1 wherein the gel base comprises by weight of said gel base from about 0.2 to about 10% of the gel-forming agent on an anhydrous basis; water in an amount effective to gel said gel-forming agent; and from about 0.2 to about 5% perfume as the air treating constituent.

3. The composition of claim 2 wherein the aqueous gel base further comprises from about 0.01 to about 10% of a foaming agent.

4. The composition of claim 3 wherein the gel-forming agent is selected from the group consisting of carrageenan, algin, amylose, and agar.

5. The composition of claim 3 further comprising up to about 5% of a viscosity control agent.

6. The composition of claim 5 wherein the viscosity control agent is selected from the group consisting of laponite and bentonite clays, and cellulosic derivatives, locust bean gum, xanthan gum, and guar gum.

7. The composition of claim 5 wherein the viscosity control agent is carboxymethyl cellulose.

8. The composition of claim 5 wherein the viscosity control agent is xanthan gum.

9. The composition of claim 3 further comprising a functionally effective amount of one or more of the following adjuvants: humectants; gelling aids; emulsifiers; perfume fixatives; extenders; preservatives, and dye.

10. The composition of claim 3 further comprising up to about 10% freeze-thaw stabilizer.

11. The composition of claim 3 wherein the mean bubble diameter is from about 50 to about 1000 microns, the one sigma distribution being from about ±200 to about ±400 microns.

12. The composition of claim 11 wherein said gel base composition comprises from about 0.2 to about 5.0% gel forming agent selected from the group consisting of carrageenan, algin, amylose, and agar; from about 0.5 to about 2% perfume; from about 0.1 to about 2.5% foaming agent, and from about 0.1 to about 1% viscosity control agent.

13. An aqueous-based gel air-treating composition comprising (a) a gel base and (b) a gaseous component in an amount effective to provide a bulk density of said composition of from about 0.5 to about 0.9 g./cc., the gaseous component being present in the composition as substantially homogeneously dispersed bubbles having a mean diameter of from about 50 to about 1000 microns, the gel base comprising by weight of the gel base from about 0.5 to about 10% of a gel-forming agent on an anhydrous basis; from about 5 to about 95% water; from about 0.2 to about 5% of a perfume; from about 0.1 to about 5% of an anionic or nonionic surface-active agent, and from about 0.1 to about 5% of a viscosity control agent.

14. The composition of claim 13 wherein the gel-forming agent is selected from the group consisting of carrageenan, algin, amylose, and agar.

15. The composition of claim 13 wherein the gel-forming agent is carrageenan.

16. The composition of claim 14 wherein the viscosity control agent is selected from the group consisting of bentonite and laponite clays, and carboxy alkyl cellulose, hydroxyalkyl cellulose, and hydroxyalkyl alkylcellulose, the alkyl groups having from 1 to about 5 carbons.

17. The composition of claim 13 wherein the gaseous component is air.

18. The composition of claim 13 wherein the surface-active agent is selected from the group consisting of anionic and nonionic surfactants.

19. A method of making an aqueous-based gel air-treating composition, the method comprising the steps: preparing a gel base comprising gelling agent, water, and a volatile air treating constituent, the temperature of which is above its glass transition temperature, introducing a gaseous component into said gel base and accompanied by sufficient mixing energy to disperse said gaseous component within the gel base to obtain a foamed gel, and allowing the foamed gel to cool below its glass transition temperature, the gaseous component having a bubble diameter in the resulting gel composition of less than 3,000 microns.

20. A method of making an aqueous-based gel air-treating composition, the method comprising the steps: preparing a gel base comprising gelling agent, water, a foaming agent and a volatile air treating constituent, the temperature of which is above its glass transition temperature; introducing a gaseous component into said gel base; subjecting said gasified gel base to shear to obtain a foamed gel containing the gaseous component dispersed therein; forming the foamed gel into a desired shape, and allowing the shaped gel to cool to ambient, the gaseous component in the shaped composition having a mean bubble diameter of from about 50 to about 1000 microns.

21. The method of claim 20 wherein the aqueous-based gel air-treating composition has a bulk density of from about 0.5 to about 0.90 g./cc.

* * * * *